(12) United States Patent
Schuster et al.

(10) Patent No.: US 6,228,632 B1
(45) Date of Patent: May 8, 2001

(54) **LEUCINE AMINOPEPTIDASES PRODUCED RECOMBINANTLY FROM *ASPERGILLUS SOYAE***

(75) Inventors: Erwin Schuster, Bensheim-Auerbach; Bruno Sproessler, Rossdorf; Kornelia Titze, Nieder-Ramstadt; Michael Gottschalk, Ober-Ramstadt; Nguyen Quoc Khanh, Reichelsheim; Sabine Wolf, Otzberg; Hermann Plainer, Reinheim, all of (DE)

(73) Assignee: Roehm GmbH, Darmstadt (DE)

( * ) Notice: Subject to any disclaimer, the term of this patent is extended or adjusted under 35 U.S.C. 154(b) by 0 days.

(21) Appl. No.: 09/011,540
(22) PCT Filed: Apr. 1, 1996
(86) PCT No.: PCT/EP96/01430
§ 371 Date: Apr. 20, 1998
§ 102(e) Date: Apr. 20, 1998
(87) PCT Pub. No.: WO97/04108
PCT Pub. Date: Feb. 6, 1997

(30) Foreign Application Priority Data

Jul. 20, 1995 (DE) ................................. 195 26 485

(51) Int. Cl.$^7$ ............... C12N 9/48; C12N 1/20; C12N 1/14; C12N 15/00; C07H 21/04
(52) U.S. Cl. .............. 435/212; 536/23.2; 435/320.1; 435/252.3; 435/254.11; 435/254.3; 435/254.6; 435/219
(58) Field of Search .................. 435/219, 320.1, 435/252.3, 254.11, 254.3, 254.6; 536/23.2

(56) References Cited

U.S. PATENT DOCUMENTS 5,200,313 * 4/1993 Carrico ....................................... 435/6
5,994,113 * 11/1999 Kauppinen et al. .................. 435/212

FOREIGN PATENT DOCUMENTS

WO 96/28542    9/1996 (WO).

OTHER PUBLICATIONS

Sambrook et al. Molecular Cloning, A Laboratory Manual, 2nd edition, pp. 9.47–9.51, 1989.*
Chemical Abstracts, vol. 85, No. 17, Oct. 25, 1976, Columbus, Ohio, Abstract No. 121828, Nakadai, Tadanobu et al, "Leucine aminopeptidase II", XP002008935 & JP A,51,063 987.
Database WPI, Section Ch, Week 7629, Derwent Publications Ltd., London, GB, Class B04, AN76–55101X, XP002008936 & JP,A,51 063 987 (Noda Sangyo Kagaku), 3, Jun. 1976.
Database WPI, Section Ch, Week 9130, Derwent Publications Ltd., London, GB; Class D13, AN 91–220330 XP002008937 & JP A,03 143 394 (Shokuhin Sangyo Bioreactor), Jun. 18, 1991.
Journal of Biological Chemistry, vol. 267, No. 12, 1992, MD US, pp. 8390–8395, XP002008934 Guenet CH et al, "Isolation of the leucine aminopeptidase gene from aeromonas proteolytica".

* cited by examiner

*Primary Examiner*—Karen Cochrane Carlson
*Assistant Examiner*—Devesh Srivastava
(74) *Attorney, Agent, or Firm*—Burns, Doane, Swecker & Mathis, L.L.P.

(57) ABSTRACT

This invention relates to a recombinant deoxyribonucleic acid (DNA) which can be isolated from *Aspergillus soyae*, characterised in that it codes for a leucine aminopeptidase (LAP) and comprises a nucleotide sequence corresponding to the nucleotide sequence given in SEQ ID NO: 1 for the mature LAP or to a nucleotide sequence derived therefrom which hybridises under stringent conditions with the nucleotide sequence given in SEQ ID NO: 1 for the mature LAP. The invention further relates to vectors and transformed host organisms, and also relates to methods of producing LAP. Enzyme products for the production of protein hydrolysates, as well as protein hydrolysates which are produced correspondingly, also form part of the invention.

18 Claims, 1 Drawing Sheet

Figure 1:
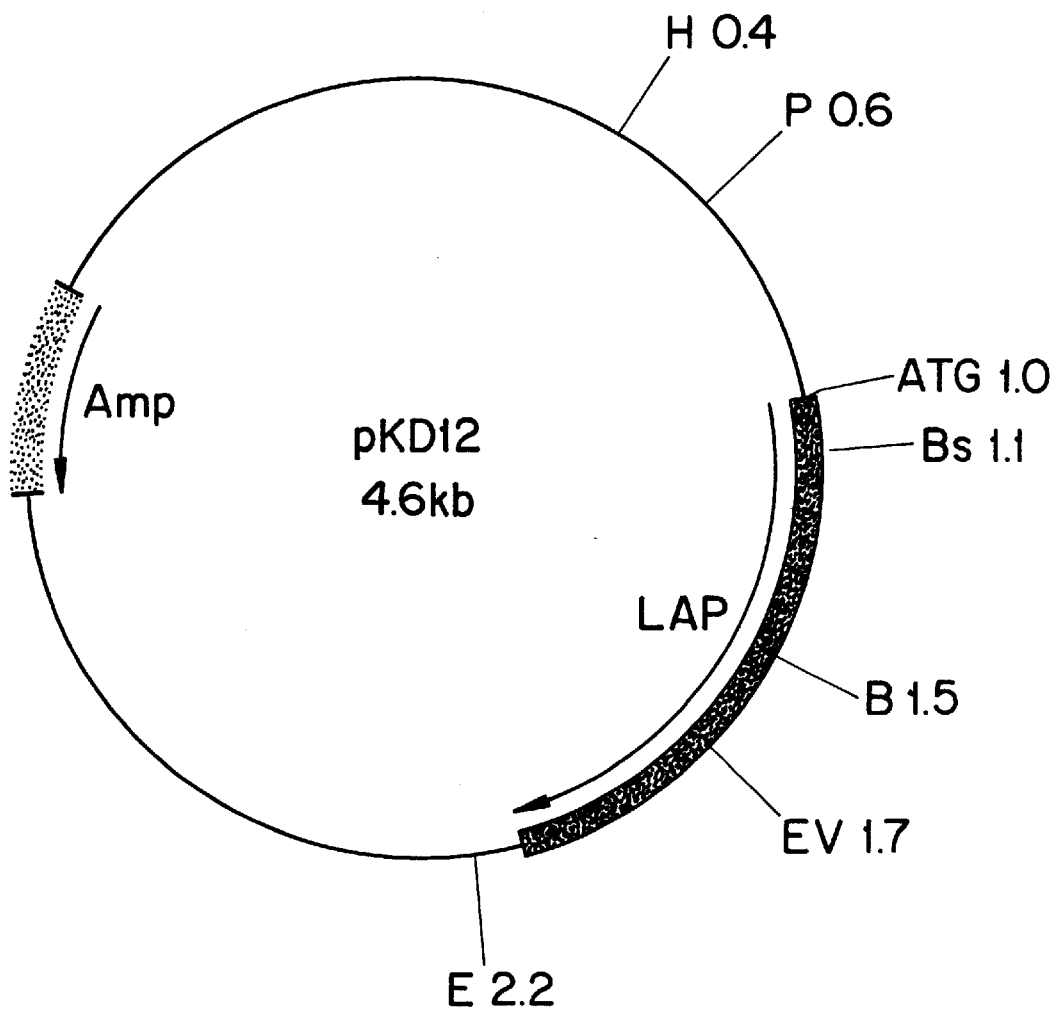

EV = EcoRV
Bs. = BstEII
E. = EcoRI
H. = HindIII
P. = PstI
B. = BamHI

LEUCINE AMINOPEPTIDASES PRODUCED RECOMBINANTLY FROM *ASPERGILLUS SOYAE*

FIELD OF THE INVENTION

This invention relates to a recombinant deoxyribonucleic acid (DNA) from *Aspergillus soyae* which codes for a leucine aminopeptidase (LAP), to vectors which contain said DNA as well as further DNA sequences for the expression of the LAP gene, and to filamentous fungi which are transformed with said vectors and which can express the recombinant DNA. The invention also relates to enzyme products which contain a recombinant LAP produced by means of the recombinant filamentous fungi and to methods of producing protein hydrolysates with a low content of bitter substances by means of the recombinant LAP.

PRIOR ART

Protein hydrolysates which are produced enzymatically from difficultly digestible or difficultly soluble animal or vegetable protein, such as gluten, or whey or soya proteins, could have a broad range of application in the food industry, e.g. as additives for whipped foodstuffs, baby foods or animal feedstuffs, and could be of general use for meat and pasta products.

One general problem is that peptides with an unpleasantly bitter accompanying taste are formed as the degree of hydrolysis of the proteins increases. Numerous attempts have already been made to eliminate this bitter accompanying taste. None of the methods developed hitherto has been completely satisfactory, so that a broad range of use has hitherto not existed.

According to more recent findings, the bitter taste is caused by a content of oligopeptides which are formed by endopeptidases as progressive cleavage of the native proteins takes place.

This bitter taste first occurs after a certain degree of hydrolysis of the peptide bonds which are contained. This critical degree of hydrolysis is therefore termed the bitter point. The bitter point is stongly dependent on the hydrolysed protein. Termination of hydrolysis before the bitter point is reached is difficult to achieve technically, and moreover has the effect that the better utilisation capacity which is the aim of hydrolysis is not achieved to its full extent.

European Patent Specification EP 384 303 describes a method of producing protein hydrolysates with a low content of bitter substances. A proteinase (endopeptinase) and an aminopeptidase (exopeptidase) from an Aspergillus culture are used for hydrolysis, in a one- or two-step process. Toxicologically harmless strains of Aspergillus species, for example, *A. oryzae, A. niger* or *A. soyae*, are cited as the source for the peptidase mixture. An excessive formation of bitter-tasting oligopeptides is prevented by restricting the proportion of endopeptidase in relation to aminopeptidase. This is effected by the selective thermal deactivation of the endopeptidases. Using this method, it is possible to delay the occurrence of the bitter point and thus to achieve higher degrees of hydrolysis whilst maintaining a low content of bitter substances.

An improvement has in fact been achieved by said method, but much higher degrees of proteolysis without the simultaneous formation of bitter peptides would be desirable commercially. Another disadvantage is that the thermal deactivation of endopeptidases, and thus the subsequent protein hydrolysis, is not completely reproducible. This applies in particular when the aim is only to effect a partial endopeptidase deactivation by a single-stage process. The poor reproducibility can result in the bitter point being exceeded, or in insufficient hydrolysis. It should also be stated that the deactivation step which has to be performed contributes to a not inconsiderable increase in the cost of the enzyme used and thus of the method as a whole.

In recent years, a series of genes for fungal proteases has been isolated and expressed. WO 90/00192 describes the isolation of the gene for Aspergillopepsin A from *A. awamori*. Aspergillopepsin is a protease which can result in the proteolytic breakdown of an external protein, paticularlyon heterologous gene expression in *A. awamori*. During the expression of calf chymosin in *A. awamori*, the problem also arises that the aspergillopepsin can give rise to unwanted off-tastes during the production of cheese. The object of the aforementioned patent application was therefore the deactivation of the unwanted gene.

Japanese Patent Application JP 90-269370 describes the isolation of the gene for alkaline protease (I) from a chromosomal gene bank of *A. soyae*. This alkaline protease is widely used in the south-east Asia region for the production of soy sauce. However, the present invention does not relate to the production of soy sauce.

OBJECT AND SOLUTION

The object of the present invention was to provide a cost-effective source of an endopeptidase for protein hydrolysis, the use of which further delays the occurrence of the bitter point by a large extent compared with the current state of the art, so that process reliability is significantly improved and costs are reduced at the same time. This object is achieved by a recombinant deoxyribonucleic acid (DNA) which can be isolated from *Aspergillus soyae*, characterised in that it codes for a leucine aminopeptidase (LAP) and comprises a nucleotide sequence corresponding to the nucleotide sequence given in SEQ ID NO: 1 for the mature LAP or to a nucleotide sequence derived therefrom which hybridises under stringent conditions with the nucleotide sequence given in SEQ ID NO: 1 for the mature LAP.

Vectors, particularly plasmids, with which Aspergillus strains or *Trichoderma reesei* strains can be transformed, can be produced by means of this DNA. Those strains which express and secrete LAP in large amounts can then be selected from the transformants obtained. These transformed host organisms in turn enable processes to be carried out for the production of LAP in large amounts. Enzyme products which contain LAP and which are particularly suitable for the hydrolysis of proteins can be produced from the fermentation liquors obtained. Surprisingly, it has been found that protein hydrolysis with the enzyme products according to the invention makes it possible to achieve degrees of hydrolysis, without the occurrence of a bitter taste, which are considerably higher than those which are possible with preparations produced in a conventional manner.

FIGURES, SEQUENCE DESCRIPTIONS AND DEPOSITION OF STRAINS

FIG. 1: Representation of the vector pKD12

Sequence descriptions:

SEQ ID NO: 1: Chromosomal LAP gene from *A. soyae* RH3782

SEQ ID NO: 2: Protein sequence of the LAP from *A. soyae* RH3782 with signal peptide sequence Deposition of strains:

The following microorganisms were deposited at the German Collection of Microorganisms and Cell Cultures (DSM), Mascheroder Weg 1b, D-38124 Brunswick, Germany, in accordance with the conditions of the Budapest Agreement (the date of deposition is given in parentheses in each case):

- A. soyae RH3782: deposition number DSM 10090 (Jul. 5, 1995)
- E. coli DH5α pKD12: deposition number DSM 10089 (Jul. 7, 1995)
- A. awamori RH3827: deposition number DSM 10091 (Jul. 5, 1995)

DESCRIPTION OF THE INVENTION

Recombinant DNA

This invention relates to a recombinant deoxyribonucleic acid (DNA) which can be isolated from Aspergillus soyae, characterised in that it codes for a leucine aminopeptidase (LAP) and comprises a nucleotide sequence corresponding to the nucleotide sequence given in SEQ ID NO: 1 for the mature LAP or to a nucleotide sequence derived therefrom which hybridises under stringent conditions with the nucleotide sequence given in SEQ ID NO: 1 for the mature LAP.

Sequence description SEQ ID NO: 1 corresponds to the chromosomal LAP gene from A. soyae RH3782 with 5'- and 3'-flanking sequences. The nucleotide sequence for the mature LAP is to be understood as the DNA sequence which is contained in SEQ ID NO: 1 and which codes for the structural gene of LAP without the signal peptide. The nucleotide sequence for the mature LAP are thus those exon sequences which code for amino acids 1 (Tyr) to 298 (Leu).

The present invention also relates to a nucleotide sequence derived from the nucleotide sequence for the mature LAP. This is to be understood to comprise nucleotide sequences which differ from the nucleotide sequence given in SEQ ID NO: 1, but which hybridise under stringent conditions with the DNA for the LAP.

The term "stringent hybridisation conditions" is familiar to one skilled in the art (see, for example, Maniatis et al. (1982): Molecular Cloning, A Laboratory Manual, Cold Spring Harbor Laboratory, New York). Stringent hybridisation conditions are those conditions under which only DNA molecules with a high degree of homology, e.g. >85%, hybridise with each other. The stringency of the test conditions can, for example, be adjusted by the hybridisation temperature or by the salt concentration of the hybridisation solution. DNA sequences derived from the LAP structural gene may, for example, comprise differences in their nucleotide sequence without differences in their amino acid sequence, due to the degeneration of the genetic code. Slight differences in the nucleotide sequence can also result in functionally insignificant changes in the amino acid sequence of the enzyme. Substantially homologous genes which can be isolated by means of the present invention from other strains of A. soyae or from closely related Aspergillus species are therefore included. The claimed definition also includes fusion proteins which comprise parts of the LAP gene or nucleotide sequences derived therefrom which are essential for the enzymatic function of the protein.

Sequence description SEQ ID NO: 1 also contains the sequence which codes for the signal peptide which is situated in front of the nucleotide sequence for the mature LAP and which begins with amino acid −79 (Met) to −1 (Thr). The functional promoter region of the LAP gene is situated in front of the signal peptide sequence. The TAA stop codon, as well as a region which functions as a transcription terminator (nucleotides 1742–1873), are situated behind the structural gene. Sequence description SEQ ID NO: 2 represents the entire amino acid sequence of the LAP with the signal peptide.

The recombinant DNA according to the invention can be obtained by the isolation of an LAP gene from an A. soyae, e.g. from A. soyae RH3782. The LAP from a culture filtrate of the strain can be purified for this purpose. This is a critical operating step, since a method of purification first has to be developed. The LAP can be separated from the other proteins by ion exchange chromatography and gel filtration. A degree of purity must be achieved here which makes possible the unambiguous sequencing of the N-terminus of the protein or of peptides therefrom. DNA probes can be derived in the known manner from the protein fragments, by the back-translation of the genetic code. DNA probes of this type can be ordered commercially according to a model or can even be produced in the known manner with the aid of a DNA synthesiser.

The claimed DNA can be obtained from the genome of an Aspergillus strain which produces LAP, particularly of an A. soyae strain. For this purpose, RNA and/or DNA are obtained from the cell material of the Aspergillus strain. Copy DNA (cDNA) and/or genomic gene banks can be constructed therefrom with the aid of suitable vectors. For example, the phage λ EMBL3 can be used as a vector for a genomic gene bank. A cDNA gene bank can be constructed, in E. coli DH5α for example, with the plasmid pUC 18.

It is advantageous for the construction of the cDNA gene bank if the initial cell material is taken up in a medium in which the strain produces as much LAP as possible, since the content of LAP-specific mRNA is higher in this induced cell material than it is in non-induced cell material. A higher proportion of LAP-specific clones can thereby be obtained in the cDNA gene bank. Examples of suitable culture media include minimal media for fungi, to which a protein-rich primary source of nitrogen is added, e.g. powdered milk or peptone. When the maximum LAP titre is reached in the medium, the cells can advantageously be harvested by freezing the filtered-off mycelium in liquid nitrogen.

Polyadenylated mRNA can be prepared in the manner known in the art from the cell material. For this purpose, the mycelium can be homogenised, e.g. in the presence of detergents and RNase inhibitors, such as heparin, guanidimiun isocyanate or mercaptoethanol for example, and the mRNA can be obtained by phenol or phenol-chloroform extractions, optionally with the addition of isoamyl alcohol, chloroform and/or diethyl ether. The extraction mixtures may optionally contain salts or buffers or cation-chelating agents in addition, in the known manner. The mRNA can subsequently be precipitated from the aqueous phase by the addition of ethanol, or can be obtained by chromatographic methods, e.g. affinity chromatography on oligo(dT)- or oligo(dU)-sepharose. Gradient centrifugation, e.g. in a linear saccharose gradient, or agarose gel chromatography, can also be used for the further purification of the isolated mRNA.

A complementary single-strand DNA can first be produced in the known manner from the mRNA by means of a reverse transcriptase (an RNA-dependent DNA polymerase), and then a double-strand cDN can be produced with the aid of a DNA-dependent DNA polymerase. For this purpose, the mRNA is incubated with a mixture of deoxynucleoside triphosphates (dATP, dCTP, dGTP and dTTP), which are optionally radioactively labelled so as to be able subsequently to trace the result of the reaction, and a primer oligonucleotide, e.g. an oligo-dT-nucleotide, which hybridises with the poly-A end of the mRNA, and with a reverse transcriptase, e.g. the reverse Avian Myoblastosis virus (AMV) transcriptase, which produces a complementary DNA In a second step, the single-strand DNA can in turn be augmented in a complementary manner, e.g. with DNA polymerase I, to form a double-strand cDNA. The cDNA can be inserted in a vector, e.g. in the phage λgt10, with the aid of DNA linkers.

The phage clones obtained can be propagated on an agar comprising E. coli host cells. DNA from these agar plates can be transferred to nitrocellulose filters which are hybridised e.g. with a radioactively labelled DNA probe. Autoradiographs can then be produced from the nitrocellulose filters, from which the position on the agar plates of clones which contain the sought-after LAP gene or parts thereof can be derived. In this manner, corresponding cDNA phage clones can be isolated from the gene bank.

Genomic DNA can be obtained from the mycelium irrespective of the culture conditions of the cells. The cell material is preferably cultured in a complete medium for fungi, e.g. Sabourard broth. Isolation of the DNA from the cell material can be effected in the known manner by the homogenisation of the cell material in a buffer, e.g. 100 mM Tris-HCl pH 8.0, and subsequent phenol or phenol-chloroform extraction. The DNA can be precipitated from the aqueous phase by the addition of ethanol, and can optionally be further purified, e.g. by CsCl density gradient centrifugation.

The DNA can be partially cut with a restriction enzyme, e.g. Sau3A, and ligated with a vector, e.g. λEMBL3. The phage clones obtained can be propagated in E. coli host cells on agar. DNA from these agar plates can be transferred to nitrocellulose filters which are hybridised with a DNA probe, e.g. with a radioactively labelled DNA probe. Autoradiographs can then be produced from the nitrocellulose filters, from which the position on the agar plates of clones which contain the sought-after LAP gene or parts thereof can be derived. In this manner, corresponding phage clones can be isolated from the gene bank.

These DNA probes can be used for screening in gene banks. It is advantageous firstly to screen a cDNA produced from the mRNA of the host strain in a cDNA gene bank. With the aid of the specific cDNA as a probe, the chromosomal gene from the genomic gene bank can then also be identified. The identification of a specific phage clone is usually followed by subcloning into a plasmid, e.g. pBR322, pUC18 or pUC19.

Characterisation of the isolated DNA is effected in the known manner by restriction analysis and subsequent sequencing, e.g. by the Sanger method. The position of the exon and intron sequences can be determined by comparing the cDNA sequence with the sequence of the chromosomal gene. The signal peptide sequence is situated between the ATG start codon of the encoding sequence and the start of the mature protein, which can be determined by its correspondence with the N-terminal amino acid sequence which is determined.

Vectors for the Expression of LAP in Aspergillus or T. reesei Strains

The present invention relates to a vector containing a) DNA sequences for the replication of the vector in E. coli, b) DNA sequences for the expression and secretion of a polypeptide in an Aspergillus strain or in a Trichoderma reesei strain which codes for a promoter, a signal peptide sequence and optionally for a terminator, c) a DNA sequence which codes for a polypeptide and which is functionally bound to the DNA sequences according to b), characterised in that the DNA sequence according to c) comprises a nucleotide sequence corresponding to the nucleotide sequence given in SEQ ID NO: 1 for the mature LAP or to a nucleotide sequence derived therefrom which hybridises under stringent conditions with the nucleotide sequence given in SEQ ID NO: 1 for the mature LAP.

The DNA sequences according to a) are necessary so as to be able to propagate the vector DNA in E. coli, e.g. in E. coli DH5α. A DNA sequence of this type can be a phage, e.g. the phage λEMBL3, a cosmid, or preferably a plasmid. Examples of suitable plasmids include pBR322, pUC18 or pUC19, or optionally fragments of these plasmids which contain at least the "origin of replication" and a selection marker for E. coli.

The vectors also contain DNA sequences according to b), which in Aspergillus strains or in T. reesei strains result in the expression and secretion of the gene of the LAP gene according to c). These DNA sequences according to b) are operably linked to the LAP gene. For example, they may be 5'- and 3'-flanking sequences such as promoters situated 5' in front of the gene, a signal peptide sequence, or terminators situated 3' behind the gene. Examples of other functional DNA sequences which may be present include ribosome binding sites for translation, enhancers or "upstream activating sequences", or polyadenylation functions.

Signal peptide sequences are DNA sequences which code for amino acids and which are situated 5' directly in front of the structural gene. They occur with extracellular proteins and are transcribed and translated together with the structural gene. On the secretion of the protein from the cell, the signal peptide sequences are cleaved, whereby the actual "mature" protein is formed. A signal peptide sequence is thus necessary in order to effect secretion of the LAP from the host cell. A promoter and a terminator are also necessary for initiating the translation and for terminating the transcription of the gene, respectively. The promoter, the signal peptide sequence and/or the terminator may be those which occur naturally in the chromosomal.

LAP gene of A. soyae. These functional DNA sequences may also originate from other genes which are secreted in fungal strains of the Aspergillus genus or which are expressed and secreted in T. reesei.

Examples of genes which comprise suitable functional DNA sequences include the TAKA amylase A gene from A. oryzae (EP 238 023), the pectinesterase gene or the polygalacturonidase gene from A. niger (EP 388 593), the glucoamylase gene from A. awamori (EP 215 594), and the cellobiohydrolase gene 1 (cbh 1) from T. reesei (EP 244 234).

The DNA sequence according to c) contains the LAP structural gene or a DNA sequence derived therefrom. This DNA sequence may, for example, take the form of a chromosomal gene containing introns, or may take the form of a cDNA without introns, which is derived from the messenger ribonucleic acid (mRNA).

The plasmid pkD 12 is an example of a vector according to the invention (see FIG. 1). This plasmid consists of the generally known E. coli plasmid pUC19 and of a HindIII/EcoRI restriction fragment from the chromosomal DNA of A. soyae RH3782. The HindIII/EcoRI restriction fragment contains the structural gene of the LAP with the natural DNA sequence which codes for the signal peptide, as well as the natural promoter situated 5' in front of the gene and termination sequences situated 3' behind the gene. The DNA sequences situated in front of and behind the structural gene, including the signal peptide sequence, are functional, and result in expression and secretion in filamentous fungi of the genus Aspergillus, e.g. in strains of A. soyae or A. oryzae.

One skilled in the art is sufficiently aware of methods by means of which a gene can be combined with functional DNA sequences, e.g. with another promoter or with a signal peptide sequence, in a vector (see Maniatis, et al. (1982): Molecular Cloning, A Laboratory Manual, Cold Spring Harbor Laboratory, New York, for example). The nucleotide sequence for the mature LAP gene or a nucleotide sequence derived therefrom can therefore also be bound to functional sequences which differ from the functional DNA sequences which are present in pKD12, and which are suitable for the expression and secretion of the LAP in a filamentous fungus of the genus Aspergillus or in T. reesei.

Above all, functional promoter sequences are particularly important with respect to the level of expression. These are DNA sequences with a length of about 500–2000 base pairs, which are each situated 5' in front of the start codon of an Aspergillus or of a T. reesei gene.

DNA sequences such as these can be isolated as restriction fragments, for example, and can be ligated with restriction fragments of the LAP gene, including the signal peptide sequence. At the same time, incompatible cleavage sites or regions without suitable restriction cleavage sites can be bridged or replaced, e.g. by synthetically produced oligonucleotides, so that the original DNA sequence is retained. In this manner, the DNA sequence of the LAP gene, including the signal peptide sequence, can be retained unchanged and can be functionally bound to a promoter sequence which is likewise unchanged.

To increase the level of expression, the natural promoter can of course be replaced by other promoters. Numerous suitable promoters are known. For example, the TAKA-amylase promoter from *A. oryzae* (see EP 238 023) is suitable for expression in *A. oryzae* or *A. soyae* strains, the gpdA promoter from *A. nidulans* (PUNT, et al. (1957) Gene 56, pages 117–124) is suitable for expression in *A. nidulans, A. niger, A. phoenicis, A. japonicus, A. foetidus* or *A. awamori* strains. A promoter that is suitable for expression in a *T. reesei* strain is for example the cbh1 promoter from *T. reesei* (EP-A-244 234).

The chromosomal terminator sequence according to SEQ. ID NO: 1, which occurs naturally behind the structural gene, is preferred as a terminator. Depending on the strain used for expression or on the promoter sequence used, it may be advantageous in addition to replace the natural leader sequence or the termination sequence also, in order to achieve expression and secretion which are improved even further. Examples of suitable terminators include the trpC terminator from *A. nidulans* (PUNT, et al., see above) or the pectinesterase terminator from *A. niger* (EP 388 593).

Transformed Aspergillus or Trichoderma Strains for the Commercial Production of LAP The plasmids according to the invention can be used for the transformation of Aspergillus or *Trichoderma reesei* strains. In the course of this procedure, the plasmids can be repeatedly integrated into the genome of the host strains. The productivity of LAP can be increased considerably by increasing the number of gene copies and/or by the use in addition of stronger promoters. Those transformants which exhibit particularly high productivity can be selected from a multiplicity of transformants. By promoting the productivity of LAP secondary activities, such as an unwanted endoproteinase activity, pale into insignificance at the same time. Strains transformed according to the invention are there-fore particularly suitable for the commercial production of LAP enzyme products.

Fungal strains from species which are known to have good production properties for enzymes are particularly suitable for the expression and secretion of LAP. Those which are particularly preferred are strains from the species *A. niger, A. awamori, A. phoenicis, A. japonicus, A. foetidus, A. oryzae* or *A. soyae*, as well as *T. reesei*. Suitable strains can be obtained from collections of strains which are accessible to the public, such as the ATCC, DSM, CBS or NRRL, for example. Examples of suitable host strains include *A. awamori* ATCC 11360, *A. foetidus* ATCC 10254 and ATCC 1035, *A. japonicus* 16873, *A. oryzae* NRRL 695, *A. niger* ATCC 10864, *A. phoenicis* CBS 136.52, and also *T. reesei* ATCC 26921. *A. awamori* NRRL 3112 is particularly suitable. The gene donor strain *A. soyae* RH3782 (deposited at the DSM) is also particularly suitable.

Transformation of the fungal strains can be accomplished using known methods. For example, EP 184 438 (U.S. Pat. No. 4,885,249) describes a transformation method for *A. niger*, in which the argB gene from *A. nidulans* is used as a selection marker. EP 238 023 describes, in Example 9, a transformation method for *A. oryzae* strains which is of general applicability. In this method, the plasmid p3SR2 is used with the amdS gene from *A. nidulans* as a selection marker. EP 244 234 describes the transformation of *T. reesei* with this vector. The transformation of *A. niger* with p3SR2 is described by KELLY and HYNES (1985), EMBO Journal 4, pages 475–479. The vector pAN7-1 (PUNT, et al. (1987) Gene 56, pp. 117–124) can be used preferentially for strains of species *A. niger, A. awanori, A. japonicus, A. phoenicis* and *A. foetidus*. Transformants can then be selected based on their resistance to hygromycin B.

For transformation, protoplasts are first produced from vegetative cells or from conidiospores, under the action of enzymes in an osmotically stabilised medium. The plasmid DNA to be transformed is added thereto, usually after a plurality of washing steps, in the presence of polyethylene glycol (PEG) and $CaCl_2$; this results in the uptake of the DNA in the cells. After transformation, the protoplasts are regenerated on an osmotically stabilised medium, whereupon those cells are selected which have taken up a marker gene.

Transformation of the fungal strains is preferably effected by the cotransformation method, in which a plasmid with a selection marker for Aspergillus or *T. reesei* strains and a vector according to the invention—a phage DNA or a cosmid DNA, or preferably a plasmid with the LAP gene—are added simultaneously to the cells to be transformed.

*A. awamori* NRRL 3112 can be cotransformed with the plasmids pAN7-1 and pKD12, for example. Transformants resistant to bygromycin B can be selected; these can be tested for the production of LAP in agitated flasks. The strain *A. awamori* RH3827, which has been deposited at the DSM (see above under the deposition of strains), is an example of a transformant of *A. awamori* NRRL 3112 which expresses LAP and which is obtained in this manner.

The amdS gene from *A. nidulans*, which is present on the vector p3SR2 for example, is a particularly suitable example. Aspergillus or Trichoderma strains which are transformed with this plasmid, and which previously exhibited poor growth on a minimal nutrient base with the synthetic substrate acetamide as the sole source of nitrogen, can be selected after transformation by means of a clear increase in growth. From the transformants which are obtained as a whole, those which exhibited an increased or particularly high LAP productivity then have to be selected. This selection can be made based on the LAP productivity of the transformants in agitated flasks, for example.

Method of Producing LAP by Using a Host Organism Transformed According to the Invention The transformed host strain can be incubated by submersion culture in a suitable medium. Suitable media are those in which filamentous fungi exhibit good growth, particularly those in which good formation of LAP occurs at the same time. Media which are particularly suitable are those in which it is known that the respective Aspergillus or *T. reesei* host strain exhibits good growth and at the same time forms LAP. As regards cost-effective media, the use of inexpensive natural products as nutrient base constituents is also particularly advantageous, such as maize powder or maize liquor, rye bran, wheat bran, potato dextrin, maltodextrin, potato protein, molasses, etc. The use of ammonium salts as N sources, e.g. ammonium sulphate, is also advantageous. One skilled in the art can turn to known methods for the fermentation of Aspergillus or *Trichoderma reesei* strains and can identify media which are particularly suitable by tests. A suitable medium may contain 5% maltodextrin and 5% wheat bran in tap water, for example.

The LAP can be produced by submersion fermentation. In the course of this procedure, inoculation can usually be effected via an inoculation cascade of culture tubes, or via Petri dish culture and agitated flasks, or optionally via one or more prefermenters in a main fermenter. The customary duration of fermentation is about 30 to 70 hours at about 28° Celsius under aerobic conditions. After the fermentation is stopped, the cell material is separated—e.g. by filtration—and the culture liquor which contains LAP is harvested. The culture liquor can be further processed to form liquid or dry LAP products, e.g. by spray drying or spray granulation. In this manner, LAP enzyme products can be produced which are suitable for the hydrolysis of proteins.

Protein Hydrolysis Using an LAP Enzyme Product According to the Invention

The LAP which is produced by a recombinant route according to the invention is outstandingly suitable for the hydrolysis of numerous animal or vegetable protein materials to form valuable protein hydrolysates, which have a neutral taste or a palatable taste and which are substantially free from any bitter taste. Examples of hydrolysable proteins include soya protein, gluten, grain and bean proteins, potato protein, yeast protein and other microbial proteins, haemoglobin, and meat and fish protein material. The method is preferably used for the hydrolysis of milk proteins, particularly casein and whey protein.

Hydrolysis is best conducted within the temperature range from 10 to 60° C., preferably from 25 to 45° C., over 1 to 10 hours with stirring. The initial proteins are advisedly used in a slurry or solution with a solids content of 5 to 15% by weight. The pH is generally within the range from 5 to 9.5, preferably 6 to 8.

The method can be carried out as a single- or multi-stage process. The method is preferably carried out as a single-step process, by allowing the LAP and a commercially available endo-proteinase, which is present in low concentration, to act simultaneously. 0.01 to 10 Anson units of endo-proteinase and $10^5$ to $10^7$ units of LAP are advisable per 100 g of the protein to be hydrolysed. Using the recombinant LAP, considerably higher degrees of hydrolysis can be achieved without the occurrence of bitter peptides than is possible using the conventional LAP described in EP 384 303, for instance.

When the desired degree of hydrolysis is reached, the endo-proteinase and the LAP are deactivated, advisedly by briefly heating them to about 100° C. Alternatively, it is also possible to effect deactivation by acidification to pH 3–4. A combination of both methods can also optionally be used. The protein hydrolysate can be processed in the desired manner to form foodstuffs or animal feedstuffs. It can be further processed in liquid form or after spray- or drum-drying, for example.

EXAMPLES (The percentage data given in the examples are percentages by weight unless indicated otherwise).

Example 1

Purification of LAP from *A. soyae*

100 ml of a culture filtrate of *A. soyae* RH3782 were made up to 1000 ml with distilled $H_2O$ and were subsequently clarified by centrifugation for 5 minutes at 5000 g and 25° Celsius. The sample was desalinated through a Sephadex G25 column (MERCK) in order to reduce its electrical conductivity. The enzyme solution which was collected had a conductivity of 3 mS/cm.

In a further step, ion-exchange chromatography was performed on DEAE-Fractogel (MERCK). For this purpose, 1000 ml of the desalinated enzyme solution were treated with 1000 ml buffer A (10 mM Tris-HCl pH 7.6, 10 mM Ca acetate) and were transferred, in several batches, to a DEAE-Fractogel column (height 235 mm, diameter 50 mm). The column was flushed with buffer A. Elution was effected in a continuous gradient of buffer A to buffer B (buffer A+1 M NaCl). Elution was effected at an elution rate of 4ml/min, and fractions of 20 ml each were collected.

The fractions were tested for the presence of LAP. This was effected by measuring the LAP activity. One LAP unit is defined according to this test procedure as the amount of enzyme which gives rise to a rate of hydrolysis of 1 micromole per minute in an 0.0016 molar aqueous solution of L-leucine-p-nitroanilide at pH 7.0 and 30° C.

The LAP activity was measured as follows:

0.3 ml of enzyme solution were added to 4 ml of substrate solution (0.0016 M L-leucine-p-nitroanilide: 0.021 g L-leucine-p-nitroanilide (Novabiochem Catalogue No. 03-32-0045) were dissolved in 2 ml of analytically pure dimethylsulphoxide (Merck) and made up to 50 ml with 0.05 M Tris-HCl, pH 7.0) which had previously been warmed to 30° C. The mixture was introduced into a 1 cm thick optical measuring cell. After 10 minutes, the extinction at 405 nm and at 30 degrees Celsius, compared with that of the substrate solution without enzyme, was determined in the photometer as $\Delta E_{405nm}$. For this purpose, the enzyme solution was diluted with 0.05 M Tris-HCl pH 7.0 so that extinction values within the range from 0.3 to 0.7 were obtained. The content of LAP was calculated according to the following formula:

$$LAP \text{ units} = \frac{\Delta E_{405nm} \cdot analysis\ volume\ (\text{ml}) \cdot 10^6}{9620\ volume\ enzyme\ solution\ (\text{ml}) \cdot enzyme\ conc \cdot t_{\min} \cdot d}$$

where

9620=molar extinction coefficient for leucine-p-nitroanilide, analysis volume=4.3 ml, volume of enzyme solution=0.3 ml, enzyme concentration=the dilution factor of the enzyme solution, $t_{min}$=10 minutes, d (layer thickness of the optical measuring cell)=1 cm.

Elution of the LAP commenced at about 0.1 M NaCl. The fractions containing LAP from several runs were combined, dialysed against distilled H₂O and subsequently lyophilised. The lyophilisate was taken up in 90 ml buffer A. In the next step the samples were introduced, in several batches, on to a Mono Q (Pharmacia) anion-exchange chromatography column and were again eluted in a continuous gradient of buffer A to buffer B. The major amount of LAP eluted between 120 and 180 ml NaCl. The eluate, amounting to 1888 ml, was dialysed against distilled H₂O and was subsequently lyophilised.

The lyophilisate was taken up in 52 ml buffer A and was further purified by gel chromatography, in 4 passes of 13 ml through a Sephacryl S-200 HR (Pharmacia) column. The fractions containing LAP were combined. The specific activity of the purified fractions was about 55,000 LAP units/mg protein. The purified protein exhibited a uniform band in SDS gel electrophoresis, with a molecular weight of about 37,000 daltons. The isoelectric point was at about pH 4.4. The protein which was purified in this manner was used for sequencing.

Example 2

Sequencing of LAP from *A. soyae*

The N-terminal amino acid sequence of the purified protein was determined using a gas-phase sequence determination device (Applied Biosystems Model 470A). The sequence which was determined was:

N-Tyr-Pro-Asp-Ser-Val-Gln-His-Xaa-Glu-Thr-Val-Gln-Asn-Leu-Ile-Asn-Ser-Leu-Asp-Lys-Lys-Asn-Phe-Glu-Thr-Val-Leu-Gln-Pro-Ile-Ser-Glu-Phe-His-Asn-Arg-COOH (SEQ ID NO: 3).

In addition, the purified enzyme was cleaved by means of trypsin, and the peptides obtained were separated by means of gel chromatography and were likewise sequenced. One of these tryptic peptides was denoted as T15 and was employed later for the derivation of an oligonucleotide. The amino acid sequence obtained from T15 was as follows:

N-Thr-Ile-Val-Leu-Gly-Ala-His-Gln-Asp-Ser-Ile-Asn-Leu-Asn-COOH

Example 3

Derivation and Synthesis of a DNA Probe

A partial sequence from the N-terminal amino acid sequence was used as a basis for deriving the oligonucleotide DNA probe KD5, wherein use was made of the codon usage of the pectinesterase gene from *A. niger*, which is known from EP 388 593. In the course of this procedure, the 5'-end was altered so that an SalI restriction enzyme cleavage site was obtained. The partial sequence from N-terminal amino acid sequence was as follows:

N-Thr-Val-Leu-Gln-Pro-Ile-Ser-Glu-Phe-His-Asn-COOH (SEQ ID NO: 4)

The sequence of the derived DNA probe KD5 was as follows (the position of the SalI cleavage site is underlined):

5'-CGC GTCGACA GTA CTT CAG CCC ATC TCG GAG TTC CAA AA-3' (SEQ ID NO: 5)

A partial sequence from the tryptic peptide T15 was employed as a model for DNA probe KD4. The partial sequence was as follows:

N-Leu-Gly-Ala-His-Gln-Asp-Ser-Ile-Asn-COOH

The sequence of DNA probe KD4 was as follows:

5'-CTC GGC GCG CAC CAG GAC TCC ATC AA-3' (SEQ ID NO: 6)

Synthesis of the DNA probes was effected by the phosphoramidite method of Beaucage, S. L. and Caruthers, M. H. (1981) Tetrahedron Letters 22, pages 1859–1862, by means of a DNA synthesiser (Applied Biosystems 380 A).

Example 4

Production of Induced Cell Material for the Isolation of RNA

A spore suspension in about 20 ml distilled water containing 0.85% NaCl and 0.1% Tween® was prepared from two Petri dishes containing cultures, which were 14 days old, of *A. soyae* RH3782 on potato glucose agar (MERCK). Erlenmeyer flasks of volume 1 liter, fitted with two baffles and containing 100 ml of LAP medium, were each inoculated with 1 ml of the spore suspension. The flasks were incubated for 120 hours at 28° Celsius, with agitation at 150 revolutions per minute.

LAP medium:

| 4%    | maize waste             |
|-------|-------------------------|
| 2%    | K₂HPO₄                  |
| 2%    | milk yeast (Otto Aldag) |
| 1.4%  | KH₂PO₄                  |
| 0.12% | MgCl₂ × 6H₂O            |
| 0.05% | CaCl₂                   |

The pH value was adjusted to 7.0. Sterilisation was performed for 15 minutes at 121° C. in an autoclave.

The mycelium was subsequently separated by filtration through sterile nylon filters, and was pressed for a short time between paper towels, using slight pressure, in order to remove surplus medium. The mycelium from two to four agitated flasks in each case was then introduced in portions into plastic bags, which were immediately transferred into liquid nitrogen. The frozen mycelium was stored at −80° C. for further use. The supernatant culture liquor was analysed for LAP activity and contained 686 LAP units/g.

Example 5

Preparation of RNA from the Induced Cells from Example 5

The method of Vierula P. J. and Kapoor, M. (1989) J. Biol. Chem. 264, pages 1108–1114, was used for the isolation of the RNA.

Example 6

Production of Cell Material for the Isolation of DNA

Production of cell material for the preparation of DNA was effected analogously to Example 5, except that Sabouraud broth (MERCK) was used as the medium instead of LAP medium. Denser growth was achieved in the medium used here (the supernatant culture liquor contained 208 LAP units).

Example 7

Synthesis of cDNA and Isolation of an LAP-Specific cDNA Clone

The method of Russo, et al. (1991) EMBO J. 10, pages 563–571, was used for the synthesis of cDNA. The principle of this method is based on the transcription of polyadenylated mRNA into single-strand cDNA by means of an oligo(dT) primer, EA13. This cDNA synthesis is followed by a polymerase chain reaction (PCR). This was started by means of the gene-specific oligonucleotide DNA probe KD5. The back-reaction was effected by means of the primer EA14, which comprised a partial sequence of the oligo(dT) primer EA13. The sequences of EA13 and EA14, respectively, are as follows (the restriction cleavage sites for the regions containing the enzymes XhoI and SalI are underlined):

EA13: 5'-GAC TCG AGT CGA CAT CGA (T)₂₁ A/C/G-3' (SEQ ID NO: 7)

EA14: 5'-GAC TCG AGT CGA CAT CGA TT-3 (SEQ ID NO: 8)

Conditions for the Synthesis of Single-strand cDNA:

10 μg RNA were treated, in a reaction volume of 50 μl, with 30 pmoles EA13 and 200 units M-MLV reverse transcriptase (Gibco-BRL) in 50 mM Tris-HCl pH 8.3, 5 mM $MgCl_2$, 75 mM KCl, 5 mM DTT, and 0.4 mM deoxynucleoside triphosphate (0.4 mM dATP, 0.4 mM dCTP, 0.4 mM dGTP and 0.4 mM dTTP). The duration of incubation was 45 minutes at 42° C.

Test Conditions for the PCR Reaction:

The reaction volume was 100 μl. The reaction was conducted in 20 mM Tris-HCl pH 8.4, 50 mM KCl, 1.5 mM $MgCl_2$, 0.2 mM deoxynucleoside triphosphate (0.2 mM dATP, 0.2 mM dCTP, 0.2 mM dGTP and 0.2 mM dTTP), with 70 pmoles KD5 and 5 units Taq-DNA polymerase. The batch was incubated for 20 PCR cycles (94° C., 40 sec –50° C., 2 min –72° C., 3 minutes per cycle).

The PCR products were subsequently separated by gel electrophoresis. A band was obtained in the region of 1 kb which hybridised with the oligonucleotide probe KD4. The PCR batch was precipitated with ethanol, cut with SalI and ligated with plasmid pUC 18 cut with SalI.

The plasmids were transformed into *E. coli* DH5α. After plating the reaction batch, 131 white colonies were obtained (in contrast to the blue colonies obtained with plasmids without insertions), from which the clone T128, which comprised a plasmid with an insertion of 1 kb, was selected by means of colony hybridisation with the radioactively labelled oligonucleotide probe KD4. This plasmid was denoted as pKD4. The insertion was sequenced. As expected, the amino acid sequence derived from the DNA contained the peptide sequences found on the protein sequencing of the LAP. The sequence is listed under SEQ ID NO. 1.

Example 8

Isolation of the Chromosomal LAP Gene

Chromosomal DNA from *A. soyae* was isolated by means of phenol extraction from the cell material from Example 7 and was partially cut with the restriction enzyme Sau3A. The DNA was fractionated according to size by means of saccharose gradient centrifugation. DNA from fractions containing fragments which were larger than 10 kb were cloned into the phage lambda EMBL3. About 250,000 recombinant phages were obtained, and were distributed on large agar plates (Nunc dishes) with about 15,000 phage forming units on each plate. The DNA of the phages was transferred from the plates on to corresponding nitrocellulose filters for hybridisation. The SalI cDNA fragment from plasmid pKD4 (see Example 8) was used as a probe for detecting phages which contained the chromosomal LAP gene. This probe was isolated and radioactively labelled. The nitrocellulose filters were hybridised with the labelled probe for 18 hours at 65° C. The filters were then washed twice with SSC buffer containing 0.1% SDS at 65° C. Two positive clones from the plates with the recombinant phages were detected by means of autoradiography. These clones were plated again and were rehybridised by the same method. A hybridising HindIII/BamHI fragment of size 1.8 kb from one of the clones was subcloned into plasmid pUC18. The plasmid obtained was denoted as pKD12.

The nucleotide sequence of the 1.8 kb insertion was determined and is reproduced in SEQ ID NO: 1. The presence and position of the chromosomal LAP gene was determined by comparison with the cDNA sequence and with this sequence. An upstream region of 426 length nucleotides, which functions as a promoter, is situated in front of the ATG start codon of the LAP gene. The LAP gene comprises a signal peptide sequence of 79 amino acids, which is interrupted by an intron. The structural gene contains two introns. Behind the stop codon there are 129 nucleotides which can function as a terminator.

Example 9

Methods of Transformation for Aspergillus and *Trichoderma reesei* Strains

A spore suspension of a Petri dish culture, which was about two weeks old, of the fungal strain to be transformed, was prepared in about 10 ml of 0.85% NaCl by floating it off using a spatula. Four one-liter agitated flasks containing 100 ml Czapek-Dox minimal medium (Oxoid) with 0.1% yeast extract were each inoculated with 1 ml of the spore suspension, and were incubated for about 16 hours at 28° C. on a rotary agitator at 120 revolutions per minute. The mycelium from four agitated flasks in each case was harvested using a paper filter and was washed with about 50 ml MP buffer (1.2 $MgSO_4$ in 10 mM phosphate buffer, pH 5.8). After the buffer had drained off, the moist mycelium was weighed. As a rule, about 3 to 5 g of moist mycelium was obtained.

5 ml MP buffer, 120 μl Novozym solution (1 g Novozym® 234 (Novo Nordisk) in 6 ml MP buffer), and 25 μl β-glucuronidase (Sigma) were added per g of moist mycelium. The mycelium suspension was placed in iced water for 5 minutes. 60 μl of bovine serum albumin solution (0.2 g bovine serum albumin in 4 ml MP buffer, sterile-filtered) were then added and the batch was incubated at 30° C. whilst being agitated slightly. The formation of protoplasts was followed visually under the microscope. When no significant increase in the formation of protoplasts was observed any longer, the incubation of the batch was terminated in order to harvest the protoplasts. This situation generally occurred after about 3 to 5 hours. The protoplast suspension was passed through a glass wool filter impregnated with MP buffer and was transferred to centrifuge tubes in order to separate any coarse mycelium constituents which were still present. The upper half of the tube was covered with 600 mM sorbitol, 100 mM Tris-HCl pH 7.0. The tubes were centrifuged for 10 minutes at 2500 g. The protoplasts were removed from the intermediate layer and were taken up in 1 M sorbitol, 10 mM Tris-HCl pH 7.5. The protoplasts were subsequently washed twice with STC buffer (1M sorbitol, 10 mM Tris-HCl pH 7.5, 10 mM $CaCl_2$) by centrifugation at 1500 g and were finally taken up in 1 ml STC buffer.

For the transformation of *A. oryzae* or *A. soyae*, 300 μl of protoplast suspension, about 10 μg p3SR2 as the selection plasmid, and 10 μg of the respective plasmid for the expression of LAP were mixed together in 25 μl 10 mM Tris-HCl pH 8.0 and were incubated for 10 minutes at 0° C. 25 μl of the same amount of DNA and 400 μl PEG solution (60% polyethylene glycol 6000 (Fluka) in 10 mM Tris-HCl pH 7.5, 50 mM $CaCl_2$) were then added together again, mixed very carefully and incubated for 5 minutes at room temperature. 600 μl PEG solution was again added, mixed, and the batch was incubated for a further 20 minutes at room temperature. The batch was mixed with about 9 ml acetamide-soft agar (a minimal medium containing 10 mM acetamide as the sole source of N, 1 M saccharose, and 0.6% by weight agar) at 45° C. and was distributed on four Petri dishes containing the same medium but with 1.5% by weight agar (Oxoid) and with 15 mM CsCl in addition. The plates were incubated at 28° C. After 6–10 days, rapidly growing colonies (transformants) were isolated on an acetamide medium without saccharose, were purified twice by way of single-spore colonies, and were finally transferred to a complete medium, e.g. potato dextrose-agar.

Transformation of strains of the species *A. niger, A. awamori, A. foetidus, A. japonicus* or *A. phoenicis* can also be effected with the plasmid p3SR2. However, transformation was preferably effected with the plasmid pAN7-1. Preparation of the protoplasts and the addition of plasmid DNA were effected in an analogous manner to that described above for the plasmid p3SR2. Instead of adding acetamide-soft agar, however, the entire transformation batch was added to 100 ml Czapek-Dox minimal medium (Oxoid) together with 100 µg hygromycin B/ml, 1.5% by weight agar (Oxoid) and 1 M saccharose, cooled to about 45 degrees Celsius, and carefully mixed. The batch was then added, in 10 ml portions each time, to Petri dishes, into each of which 10 ml Czapek-Dox minimal medium (Oxoid) had been introduced together with 1.5% by weight agar (Oxoid), but without hygromycin and without saccharose, as a solid lower layer. After solidification of the upper agar layer, the Petri dishes were incubated at 37 degrees Celsius. Transformants resistant to hygromycin B could be removed after 3–10 days and were transferred to Czapek-Dox minimal medium (Oxoid) containing 50 µg hygromycin B/ml and 1.5% by weight agar (Oxoid) in order to test their resistance.

Example 10

Production of a Transformant which Secretes LAP

The strain *A. awamori* NRRL 3112 was cotransformed with pAN7-1 and pKD12 as in Example 9. A multiplicity of transformants was obtained which were resistant to hygromycin B, and these were tested for the production of LAP in agitated flasks using the LAP medium described in Example 4. In several tests, the supernatant culture liquors of the *A. awamori* RH 3827 transformants contained 5000–10,000 LAP units/ml. The strain was deposited at the DSM.

What is claimed is:

1. A recombinant deoxyribonucleic acid (DNA) which can be isolated from *Aspergillus soyae*, which codes for a leucine aminopeptidase (LAP) and (i) comprises the nucleotide sequence SEQ ID NO: 1 which encodes mature LAP or (ii) a nucleotide sequence that is 85% identical to the nucleotide sequence of SEQ ID NO: 1, over the entire sequence, and which encodes a mature LAP, wherein said nucleotide sequence (i) or (ii) contains an asparagine codon at position 104, and an arginine codon at position 283.

2. A vector comprising
   a) DNA sequences that provide for the replication of said vector in *E. coli*,
   b) DNA sequences that provide for the expression and secretion of a polypeptide in an Aspergillus strain or in a *Trichoderma reesei* strain, which sequences include a promoter, a signal peptide sequence and optionally a terminator,
   c) the recombinant DNA sequence of claim 1, which encodes leucine amino peptidase (LAP), polypeptide and which is operably linked to the DNA sequences of b).

3. A vector according to claim 2, wherein said vector is a plasmid.

4. A vector according to claim 3, wherein said vector is the plasmid pkD12.

5. A vector according to claim 2, wherein said vector is a phage or cosmid.

6. A vector according to claim 2, wherein the promoter DNA sequences according to b) are selected from the group consisting of TAKA-amylase A promoter, the gpdA promoter from *Aspergillus nidulans*, the pectinesterase promoter from *Aspergillus niger*, the polygalacturonidase promoter from *Aspergillus niger*, the glucoamylase promoter from *Aspergillus niger* or *Aspergillus awamori*, the leucine aminopeptidase promoter from *Aspergillus soyae*, and the cellobiohydrolase (cbhl) promoter from *Trichoderma reesei*.

7. A vector according to claim 2, wherein said signal peptide DNA sequences according to b) are selected from the group consisting of the TAKA-amylase A signal peptide sequence, the pectinesterase signal peptide sequence from *Aspergillus niger*, the polygalacturonidase signal peptide sequence from *Aspergillus niger*, the glucoamylase signal peptide sequence from *Aspergillus niger* or *Aspergillus awamori*, the leucine aminopeptidase signal peptide sequence from *Aspergillus soyae*, and the cellobiohydrolase signal peptide sequence (cbhl) from *Trichoderma reesei*.

8. A transformed host organism which produces leucine aminopeptiase when cultured under appropriate conditions, wherein said transformed host organism is an Aspergillus strain or a *Trichoderma reesei* strain which has been transformed with a vector according to claim 2.

9. A transformed host organism according to claim 8, wherein said host organism is selected from the group consisting of a strain of *Aspergillus niger, Aspergillus awamori, Aspergillus foetidus, Aspergillus japonicus, Aspergillus phoenicis, Aspergillus oryzae, Aspergillus soyae* and *Trichoderma reesei*.

10. A transformed host organism according to claim 9, wherein said host organism is *Aspergillus soyae* RH3782.

11. A method of producing leucine aminopeptidase comprising (i) culturing a transformed host organism according to claim 8 in a suitable culture medium and (ii) recovering secreted leucine aminopeptidase from the resultant cell-free culture filtrate.

12. A method according to claim 11, wherein said transformed host organism is selected from the group consisting of a strain of *Aspergillus niger, Aspergillus awamori, Aspergillus foetidus, Aspergillus japonicus, Aspergillus phoenicis, Aspergillus oryzae, Aspergillus soyae* and *Trichoderma reesei*.

13. A method according to claim 12, wherein said transform host organism is *Aspergillus soyae* RH3782.

14. A method according to claim 12, wherein said transformed host organism is *Aspergillus awamori* RH3827.

15. An enzyme product suitable for protein hydrolysis, which comprises a leucine aminopeptidase produced using a recombinant Aspergillus or *Trichoderma reesei* strain that expresses a DNA according to claim 1.

16. An enzyme product according to claim 15, wherein the leucine aminopeptidase is produced by expression of a recombinant deoxyribunucleic acid (DNA) having the nucleotide sequence given in SEQ ID NO: 1 encoding mature LAP, or to a nucleotide sequence which hybridizes under stringent conditions with the nucleotide sequence given in SEQ ID NO: 1 and encodes mature LAP, wherein stringent conditions are conditions such that the hybridizing DNA has a nucleotide sequence wherein at least 85% of the nucleotides are identical to SEQ ID NO: 1.

17. A protein hydrolyzate, which is produced using the enzyme product of claim 15.

18. An isolated DNA molecule which has SEQ ID NO: 1 or a DNA encoding the polypeptide having the amino acid sequence encoded by SEQ ID NO: 1.

* * * * *

SEQUENCE LISTING

```
<160> NUMBER OF SEQ ID NOS: 12

<210> SEQ ID NO: 1
<211> LENGTH: 1873
<212> TYPE: DNA
<213> ORGANISM: Aspergillus sojae
<220> FEATURE:
<221> NAME/KEY: intron
<222> LOCATION: (1065)..(1132)
<220> FEATURE:
<221> NAME/KEY: exon
<222> LOCATION: (1133)..(1450)
<220> FEATURE:
<221> NAME/KEY: intron
<222> LOCATION: (1451)..(1507)
<220> FEATURE:
<221> NAME/KEY: exon
<222> LOCATION: (1508)..(1741)
<220> FEATURE:
<221> NAME/KEY: CDS
<222> LOCATION: (427)..(579)
<220> FEATURE:
<221> NAME/KEY: CDS
<222> LOCATION: (639)..(1064)
<220> FEATURE:
<221> NAME/KEY: CDS
<222> LOCATION: (1133)..(1450)
<220> FEATURE:
<221> NAME/KEY: CDS
<222> LOCATION: (1508)..(1741)
<220> FEATURE:
<221> NAME/KEY: mat_peptide
<222> LOCATION: (723)..(1741)
<220> FEATURE:
<221> NAME/KEY: sig_peptide
<222> LOCATION: (427)..(579)
<220> FEATURE:
<221> NAME/KEY: intron
<222> LOCATION: (580)..(638)
<220> FEATURE:
<221> NAME/KEY: sig_peptide
<222> LOCATION: (639)..(722)
<220> FEATURE:
<221> NAME/KEY: misc_feature
<222> LOCATION: (993)..(1034)
<223> OTHER INFORMATION: product: codons for tryptic peptide T15
<220> FEATURE:
<221> NAME/KEY: exon
<222> LOCATION: (427)..(579)
<220> FEATURE:
<221> NAME/KEY: exon
<222> LOCATION: (639)..(1064)
```

```
<220> FEATURE:
<221> NAME/KEY: misc_feature
<222> LOCATION: (1002)..(1028)
<223> OTHER INFORMATION: product: KD4 probe

<400> SEQUENCE: 1
aagcttggca gggcgggttc cctacggacc cccggcgggg aatccctgat gtatccatgc      60
tttctcatct gatagggttg gagacagtag atcttcatca cctccgattt ccttcctcaa     120
gatcccatga cttcaggtta caatggtctc tgcagataca gcttacttcc cggcattata     180
ggaaggtcgg agaggtgcca agtgttgcca agcagctcct catatcttgc atcatacttg     240
gcccggaata ttctatggcg tcaaatgtaa tacaccgtac cttgccatgt gactaattcg     300
ctggtctata aaacctcgag ttctgtcttt ccataaagtg gatcgttccc tcataatcag     360
tctccctcgg ctactcgagc attccgttcg tatcgacttg gtgatacacg cttttgttcg     420 ctcaat atg cgt ttc ctc ccc tgc atc gcg acc ttg gca gcc acg gcc        468
       Met Arg Phe Leu Pro Cys Ile Ala Thr Leu Ala Ala Thr Ala
               -75                 -70 tct gcc ctt gct att gga gac cat atc cgt tcg gac gat cag tat gtc      516
Ser Ala Leu Ala Ile Gly Asp His Ile Arg Ser Asp Asp Gln Tyr Val
-65                 -60                 -55                 -50 cta gaa ctt ggc ccg gga gaa acg aaa gtt gtt acg gaa gca gag aaa      564
Leu Glu Leu Gly Pro Gly Glu Thr Lys Val Val Thr Glu Ala Glu Lys
            -45                 -40                 -35 tgg gct ctg agg gct gtatgacgaa atttcccttt gacgtttacg cccagcatcc     619
Trp Ala Leu Arg Ala
            -30 cgctaataag attgaacag gag ggc aag cgt ttt ttc gat ata act gga cgg     671
                     Glu Gly Lys Arg Phe Phe Asp Ile Thr Gly Arg
                                 -25                 -20 acc agt agc ctg gaa ctc gca tcg aac aag aag caa aaa ctc gcg gtc      719
Thr Ser Ser Leu Glu Leu Ala Ser Asn Lys Lys Gln Lys Leu Ala Val
            -15                 -10                 -5 acc tat ccc gat tcc gtg caa cat aac gag acc gtg caa aac cta atc      767
Thr Tyr Pro Asp Ser Val Gln His Asn Glu Thr Val Gln Asn Leu Ile
-1   1               5                  10                  15 aac tcg ctc gac aaa aag aac ttt gaa acc gtt ctc cag ccg ttc tcg      815
Asn Ser Leu Asp Lys Lys Asn Phe Glu Thr Val Leu Gln Pro Phe Ser
                 20                 25                  30 gag ttc cac aat cgc tat tat aag agc gac aat ggt aag aaa tca tcc      863
Glu Phe His Asn Arg Tyr Tyr Lys Ser Asp Asn Gly Lys Lys Ser Ser
             35                 40                  45 gag tgg ctg caa ggc aag att cag gaa atc atc tcc gcc agt gga gca      911
Glu Trp Leu Gln Gly Lys Ile Gln Glu Ile Ile Ser Ala Ser Gly Ala
         50                 55                  60 aag gga gtc act gtg gag cct ttc aaa cac tcc ttc ccg cag tcg agt      959
Lys Gly Val Thr Val Glu Pro Phe Lys His Ser Phe Pro Gln Ser Ser
 65                 70                  75 ttg att gcg aag atc ccc ggc aag agt gac aaa acc atc gtt ctt gga     1007
Leu Ile Ala Lys Ile Pro Gly Lys Ser Asp Lys Thr Ile Val Leu Gly
 80                 85                  90                  95 gcg cat cag gac tcc atc aac ctc aat tcg cct tca gag ggc cgt gca     1055
Ala His Gln Asp Ser Ile Asn Leu Asn Ser Pro Ser Glu Gly Arg Ala
                100                 105                 110 cca ggt gct ggtgggtact tcgcacgtcc tgtccatgaa ccatagaaca              1104
Pro Gly Ala tcgtgatgct aacagagacg cgtggtta gat gac gat gga tcc ggt gtt gtt      1156
                                Asp Asp Asp Gly Ser Gly Val Val
```

```
acc atc ctt gaa gcc ttc cgc gtt ctc ctg acg gac gag aag gtt gcg    1204
Thr Ile Leu Glu Ala Phe Arg Val Leu Leu Thr Asp Glu Lys Val Ala
        125                 130                 135 gcc ggt gag gct ccg aac acc gtt gag ttc cac ttc tat gcc gga gag    1252
Ala Gly Glu Ala Pro Asn Thr Val Glu Phe His Phe Tyr Ala Gly Glu
    140                 145                 150 gag gga ggt ctt ctg gga agt cag gat atc ttt gag cag tac tcc cag    1300
Glu Gly Gly Leu Leu Gly Ser Gln Asp Ile Phe Glu Gln Tyr Ser Gln
155                 160                 165                 170 aaa agc cga gat gtg aaa gcc atg ctc cag cag gat atg acg ggt tat    1348
Lys Ser Arg Asp Val Lys Ala Met Leu Gln Gln Asp Met Thr Gly Tyr
                175                 180                 185 acc aaa ggc acc act gat gct gga aag cca gag tcg atc ggc atc atc    1396
Thr Lys Gly Thr Thr Asp Ala Gly Lys Pro Glu Ser Ile Gly Ile Ile
            190                 195                 200 acc gac aat gtc gat gag aac ctg acc aag ttc ctg aag gtc att gtc    1444
Thr Asp Asn Val Asp Glu Asn Leu Thr Lys Phe Leu Lys Val Ile Val
        205                 210                 215 gat gct gtaagtttca aaacctgttt gtggtagtcc cttcatgctt acactggata    1500
Asp Ala
    220 cttgtag tat tgc act atc ccg acc gtc gat tcg aaa tgc gga tac gga    1549
        Tyr Cys Thr Ile Pro Thr Val Asp Ser Lys Cys Gly Tyr Gly
                        225                 230 tgc tct gac cat gct tct gcc acg aag tat ggt tat ccc gcc gca ttt    1597
Cys Ser Asp His Ala Ser Ala Thr Lys Tyr Gly Tyr Pro Ala Ala Phe
235                 240                 245                 250 gca ttc gag tca gcc ttt ggc gac gac agc cct tac att cac tcg gcc    1645
Ala Phe Glu Ser Ala Phe Gly Asp Asp Ser Pro Tyr Ile His Ser Ala
                255                 260                 265 gat gat acg att gag acc gtc aac ttt gac cat gtg ctg caa cac ggc    1693
Asp Asp Thr Ile Glu Thr Val Asn Phe Asp His Val Leu Gln His Gly
            270                 275                 280 aga ctg act ctt gga ttt gca tat gag ctt gcc ttc gca gat tca ctg    1741
Arg Leu Thr Leu Gly Phe Ala Tyr Glu Leu Ala Phe Ala Asp Ser Leu
        285                 290                 295 taaggcttat gatgacggtt gtatgagcga gagatccagt ccaacagtgt gtataatatg    1801
tgggcctgtg ttcaaatagc actttgattt agcccgcgat tagctttcgt gacgaaaata    1861
gaggccgaat tc                                                        1873

<210> SEQ ID NO: 2
<211> LENGTH: 377
<212> TYPE: PRT
<213> ORGANISM: Aspergillus sojae

<400> SEQUENCE: 2

Met Arg Phe Leu Pro Cys Ile Ala Thr Leu Ala Ala Thr Ala Ser Ala
                -75                 -70                 -65

Leu Ala Ile Gly Asp His Ile Arg Ser Asp Asp Gln Tyr Val Leu Glu
            -60                 -55                 -50

Leu Gly Pro Gly Glu Thr Lys Val Val Thr Glu Ala Glu Lys Trp Ala
        -45                 -40                 -35

Leu Arg Ala Glu Gly Lys Arg Phe Phe Asp Ile Thr Gly Arg Thr Ser
    -30                 -25                 -20

Ser Leu Glu Leu Ala Ser Asn Lys Lys Gln Lys Leu Ala Val Thr Tyr
-15                 -10                 -5                  -1  1
```

-continued

```
Pro Asp Ser Val Gln His Asn Glu Thr Val Gln Asn Leu Ile Asn Ser
         5                  10                  15

Leu Asp Lys Lys Asn Phe Glu Thr Val Leu Gln Pro Phe Ser Glu Phe
        20                  25                  30

His Asn Arg Tyr Tyr Lys Ser Asp Asn Gly Lys Lys Ser Ser Glu Trp
     35                  40                  45

Leu Gln Gly Lys Ile Gln Glu Ile Ile Ser Ala Ser Gly Ala Lys Gly
 50                  55                  60                  65

Val Thr Val Glu Pro Phe Lys His Ser Phe Pro Gln Ser Ser Leu Ile
                 70                  75                  80

Ala Lys Ile Pro Gly Lys Ser Asp Lys Thr Ile Val Leu Gly Ala His
             85                  90                  95

Gln Asp Ser Ile Asn Leu Asn Ser Pro Ser Glu Gly Arg Ala Pro Gly
            100                 105                 110

Ala Asp Asp Asp Gly Ser Gly Val Val Thr Ile Leu Glu Ala Phe Arg
        115                 120                 125

Val Leu Leu Thr Asp Glu Lys Val Ala Ala Gly Glu Ala Pro Asn Thr
130                 135                 140                 145

Val Glu Phe His Phe Tyr Ala Gly Glu Glu Gly Leu Leu Gly Ser
                150                 155                 160

Gln Asp Ile Phe Glu Gln Tyr Ser Gln Lys Ser Arg Asp Val Lys Ala
            165                 170                 175

Met Leu Gln Gln Asp Met Thr Gly Tyr Thr Lys Gly Thr Thr Asp Ala
        180                 185                 190

Gly Lys Pro Glu Ser Ile Gly Ile Ile Thr Asp Asn Val Asp Glu Asn
    195                 200                 205

Leu Thr Lys Phe Leu Lys Val Ile Val Asp Ala Tyr Cys Thr Ile Pro
210                 215                 220                 225

Thr Val Asp Ser Lys Cys Gly Tyr Gly Cys Ser Asp His Ala Ser Ala
                230                 235                 240

Thr Lys Tyr Gly Tyr Pro Ala Ala Phe Ala Phe Glu Ser Ala Phe Gly
            245                 250                 255

Asp Asp Ser Pro Tyr Ile His Ser Ala Asp Thr Ile Glu Thr Val
        260                 265                 270

Asn Phe Asp His Val Leu Gln His Gly Arg Leu Thr Leu Gly Phe Ala
    275                 280                 285

Tyr Glu Leu Ala Phe Ala Asp Ser Leu
290                 295

<210> SEQ ID NO: 3
<211> LENGTH: 51
<212> TYPE: PRT
<213> ORGANISM: Aspergillus sojae

<400> SEQUENCE: 3

Met Arg Phe Leu Pro Cys Ile Ala Thr Leu Ala Ala Thr Ala Ser Ala
  1               5                  10                  15

Leu Ala Ile Gly Asp His Ile Arg Ser Asp Asp Gln Tyr Val Leu Glu
             20                  25                  30

Leu Gly Pro Gly Glu Thr Lys Val Val Thr Glu Ala Glu Lys Trp Ala
        35                  40                  45

Leu Arg Ala
    50

<210> SEQ ID NO: 4
```

-continued

```
<211> LENGTH: 142
<212> TYPE: PRT
<213> ORGANISM: Aspergillus sojae

<400> SEQUENCE: 4

Glu Gly Lys Arg Phe Phe Asp Ile Thr Gly Arg Thr Ser Ser Leu Glu
 1               5                  10                  15

Leu Ala Ser Asn Lys Lys Gln Lys Leu Ala Val Thr Tyr Pro Asp Ser
             20                  25                  30

Val Gln His Asn Glu Thr Val Gln Asn Leu Ile Asn Ser Leu Asp Lys
         35                  40                  45

Lys Asn Phe Glu Thr Val Leu Gln Pro Phe Ser Glu Phe His Asn Arg
     50                  55                  60

Tyr Tyr Lys Ser Asp Asn Gly Lys Lys Ser Ser Glu Trp Leu Gln Gly
 65                  70                  75                  80

Lys Ile Gln Glu Ile Ile Ser Ala Ser Gly Ala Lys Gly Val Thr Val
                 85                  90                  95

Glu Pro Phe Lys His Ser Phe Pro Gln Ser Ser Leu Ile Ala Lys Ile
            100                 105                 110

Pro Gly Lys Ser Asp Lys Thr Ile Val Leu Gly Ala His Gln Asp Ser
        115                 120                 125

Ile Asn Leu Asn Ser Pro Ser Glu Gly Arg Ala Pro Gly Ala
    130                 135                 140

<210> SEQ ID NO: 5
<211> LENGTH: 106
<212> TYPE: PRT
<213> ORGANISM: Aspergillus sojae

<400> SEQUENCE: 5

Asp Asp Asp Gly Ser Gly Val Val Thr Ile Leu Glu Ala Phe Arg Val
 1               5                  10                  15

Leu Leu Thr Asp Glu Lys Val Ala Ala Gly Glu Ala Pro Asn Thr Val
             20                  25                  30

Glu Phe His Phe Tyr Ala Gly Glu Glu Gly Leu Leu Gly Ser Gln
         35                  40                  45

Asp Ile Phe Glu Gln Tyr Ser Gln Lys Ser Arg Asp Val Lys Ala Met
     50                  55                  60

Leu Gln Gln Asp Met Thr Gly Tyr Thr Lys Gly Thr Thr Asp Ala Gly
 65                  70                  75                  80

Lys Pro Glu Ser Ile Gly Ile Thr Asp Asn Val Asp Glu Asn Leu
                 85                  90                  95

Thr Lys Phe Leu Lys Val Ile Val Asp Ala
            100                 105

<210> SEQ ID NO: 6
<211> LENGTH: 78
<212> TYPE: PRT
<213> ORGANISM: Aspergillus sojae

<400> SEQUENCE: 6

Tyr Cys Thr Ile Pro Thr Val Asp Ser Lys Cys Gly Tyr Gly Cys Ser
 1               5                  10                  15

Asp His Ala Ser Ala Thr Lys Tyr Gly Tyr Pro Ala Ala Phe Ala Phe
             20                  25                  30

Glu Ser Ala Phe Gly Asp Asp Ser Pro Tyr Ile His Ser Ala Asp Asp
         35                  40                  45
```

```
Thr Ile Glu Thr Val Asn Phe Asp His Val Leu Gln His Gly Arg Leu
         50                  55                  60

Thr Leu Gly Phe Ala Tyr Glu Leu Ala Phe Ala Asp Ser Leu
 65                  70                  75
```

<210> SEQ ID NO: 7
<211> LENGTH: 36
<212> TYPE: PRT
<213> ORGANISM: Aspergillus sojae

<400> SEQUENCE: 7

```
Tyr Pro Asp Ser Val Gln His Xaa Glu Thr Val Gln Asn Leu Ile Asn
  1               5                  10                  15

Ser Leu Asp Lys Lys Asn Phe Glu Thr Val Leu Gln Pro Ile Ser Glu
                 20                  25                  30

Phe His Asn Arg
             35
```

<210> SEQ ID NO: 8
<211> LENGTH: 11
<212> TYPE: PRT
<213> ORGANISM: Aspergillus sojae

<400> SEQUENCE: 8

```
Thr Val Leu Gln Pro Ile Ser Gly Phe His Asn
  1               5                  10
```

<210> SEQ ID NO: 9
<211> LENGTH: 39
<212> TYPE: DNA
<213> ORGANISM: Aspergillus sojae

<400> SEQUENCE: 9
cgcgtcgaca gtacttcagc ccatctcgga gttccaaaa         39

<210> SEQ ID NO: 10
<211> LENGTH: 26
<212> TYPE: DNA
<213> ORGANISM: Aspergillus sojae

<400> SEQUENCE: 10
ctcggcgcgc accaggactc catcaa         26

<210> SEQ ID NO: 11
<211> LENGTH: 40
<212> TYPE: DNA
<213> ORGANISM: Aspergillus sojae
<220> FEATURE:
<221> NAME/KEY: misc_feature
<222> LOCATION: (39)..(40)
<223> OTHER INFORMATION: N is A, C or G.

<400> SEQUENCE: 11
gactcgagtc gacatcgatt tttttttttt ttttttttn         40

<210> SEQ ID NO: 12
<211> LENGTH: 20
<212> TYPE: DNA
<213> ORGANISM: Aspergillus sojae

<400> SEQUENCE: 12
gactcgagtc gacatcgatt         20